(12) United States Patent
Bureiko et al.

(10) Patent No.: US 7,887,600 B2
(45) Date of Patent: Feb. 15, 2011

(54) GEL NETWORK SURFACTANT BASED THICKENING SYSTEMS FOR HAIR COLOURANT AND BLEACHING COMPOSITIONS

(75) Inventors: Andrei Sergeevich Bureiko, Sunningdale (GB); Ashok Saggi, Feltham (GB)

(73) Assignee: The Procter & Gamble Company, Cincinnati, OH (US)

( * ) Notice: Subject to any disclaimer, the term of this patent is extended or adjusted under 35 U.S.C. 154(b) by 542 days.

(21) Appl. No.: 11/827,159

(22) Filed: Jul. 11, 2007

(65) Prior Publication Data

US 2008/0010754 A1 Jan. 17, 2008

(30) Foreign Application Priority Data

Jul. 12, 2006 (EP) ................. 06117054

(51) Int. Cl.
*A61Q 5/10* (2006.01)
(52) U.S. Cl. ............ 8/405; 8/406; 8/435; 8/552; 8/554; 8/107; 8/111
(58) Field of Classification Search .......... 8/405, 8/406, 435, 552, 554, 107, 111
See application file for complete search history.

(56) References Cited

U.S. PATENT DOCUMENTS

| | | | |
|---|---|---|---|
| 4,566,875 | A | 1/1986 | Grollier |
| 4,776,855 | A | 10/1988 | Pohl |
| RE33,786 | E | 1/1992 | Pohl |
| 5,131,912 | A | 7/1992 | Ehara et al. |
| 6,821,302 | B2 | 11/2004 | Au et al. |
| 7,044,986 | B2 | 5/2006 | Ogawa et al. |
| 7,204,861 | B2 | 4/2007 | Marsh |
| 7,476,259 | B2 | 1/2009 | Bolton |
| 7,481,846 | B2 | 1/2009 | Marsh |
| 7,597,719 | B2 | 10/2009 | Bureiko |
| 2004/0019980 | A1 | 2/2004 | Au et al. |
| 2004/0098814 | A1 | 5/2004 | Au et al. |
| 2004/0098816 | A1 | 5/2004 | Au et al. |
| 2004/0237218 | A1* | 12/2004 | Marsh et al. .......... 8/405 |
| 2006/0117493 | A1 | 6/2006 | Bureiko |
| 2006/0117494 | A1 | 6/2006 | Marsh |
| 2006/0117498 | A1* | 6/2006 | Bureiko et al. .......... 8/406 |
| 2008/0010754 | A1 | 1/2008 | Bureiko |
| 2009/0297463 | A1 | 12/2009 | Bureiko |

FOREIGN PATENT DOCUMENTS

| | | |
|---|---|---|
| DE | 19721797 C1 | 9/1998 |
| EP | 1669 105 A1 * | 6/2006 |
| JP | 60155108 A2 | 8/1985 |
| JP | 63174917 A2 | 7/1988 |
| JP | 01165514 A2 | 6/1989 |
| JP | 03170413 A2 | 7/1991 |
| JP | 06271435 A2 | 9/1994 |
| JP | 07082123 A2 | 3/1995 |
| JP | 08157345 A2 | 6/1996 |
| JP | 09002925 A2 | 1/1997 |
| JP | 10226630 A2 | 8/1998 |
| JP | 11012140 A2 | 1/1999 |
| JP | 11199454 A2 | 7/1999 |
| JP | 2001-206825 A | 7/2001 |
| JP | 2001328926 A2 | 11/2001 |
| JP | 2002173418 A2 | 6/2002 |
| JP | 2002187826 A2 | 7/2002 |
| JP | 2002193770 A2 | 7/2002 |
| JP | 2002193772 A2 | 7/2002 |
| JP | 2002338446 A2 | 11/2002 |
| JP | 2002363048 A2 | 12/2002 |
| JP | 2003512309 T2 | 4/2003 |
| JP | 2004161707 A2 | 6/2004 |
| JP | 2004224792 A2 | 8/2004 |
| JP | 2004524333 T2 | 8/2004 |
| JP | 2004524353 T2 | 8/2004 |
| JP | 2005023023 A2 | 1/2005 |
| JP | 2005194202 A2 | 7/2005 |
| WO | WO 01/28508 A1 | 4/2001 |

* cited by examiner

*Primary Examiner*—Eisa B Elhilo
(74) *Attorney, Agent, or Firm*—Laura R. Grunzinger; Melissa G. Krasovec

(57) ABSTRACT

The present invention relates to hair coloring and hair bleaching compositions comprising a source of hydrogen peroxide, alkalizer and a specified gel network thickener system. The compositions surprisingly provide improved hair colorant and bleaching compositions which deliver improved lift, lightening and color delivery whilst minimizing damage and scalp sensory irritation which are easy to manufacture and have long shelf life stability.

16 Claims, No Drawings

GEL NETWORK SURFACTANT BASED THICKENING SYSTEMS FOR HAIR COLOURANT AND BLEACHING COMPOSITIONS

FIELD OF THE INVENTION

The present invention relates to hair colouring and hair bleaching compositions.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex where they can then react with each other and suitable oxidising agents to form the end dye molecules. Due to the larger size of these resultant molecules they are unable to readily diffuse out of the hair during subsequent washing with water and/or detergents; hence delivering a consumer-desired permanency of colour. This reaction typically takes place in an aggressive environment at approximately pH 10 in the presence of an alkalizing agent and in the presence of an oxidizing agent. Moreover, the consumer repeats this process regularly in order to maintain the desired hair colour and shade and the intensity of colour and to ensure continual, even coverage of the hair including coverage of new hair growth.

The manufacturer of such products is also required to work within a large number of constraints. Since these products are being placed in direct contact with the consumers' skin, the potential exists for accidental contact with the eye or for ingestion (for example), which can occur during the dyeing process. Therefore, the formulation must meet rigorous safety requirements and not induce any allergic reactions. In addition to meeting these requirements, the products must also be optically and olfactory pleasing to the consumer. In particular, the products also need to meet certain physical parameters in order to ensure that the product can be easily applied to the hair by the consumer to provide the desired effect, without unintentional staining of the consumers' clothes, skin particularly along the hair line or other objects.

The manufacturer is also required to provide the hair colouring consumer a large range of different resulting colours. Some consumers may just wish to enhance the natural colour of the hair, whilst others may wish to cover grey or completely alter the hair colour to a different natural appearing hair colour or a 'synthetic' appearing hair colour. Consequently, the manufacturer may provide over twenty different formulations, of varying colours and shades, to address the range of consumer specific needs. These formulations have to be individually formulated and are typically complex formulae containing a mixture of different dye compounds. As a result the manufacture of such product ranges can be costly and complex.

However, despite the fact that commercial hair dyeing products have been available for many years, the products still exhibit a number of consumer-related deficiencies. Typically permanent hair dye products will contain an alkali, typically a source of ammonia. This serves the purpose of swelling the hair allowing the entry of the dye precursor molecules into the hair and also improves the lightening effect of the oxidising agent, which is typically hydrogen peroxide. However, ammonia is also volatile and its associated odour is extremely unpleasant and often irritating to the consumers' of such products, particularly as these hair dye products are used in close proximity to the nasal region. Hence, it would be highly desirable to provide an oxidative hair colouring and/or bleaching composition, which delivers the consumer required lightening level and colour, but which has reduced or eliminated the detectable ammonia odour.

In fact another deficiency area in current hair colouring products is the provision of hair colouring products which deliver the required hair lightening effect. Delivering the required level of lightening is particularly important in order to provide the full range of colour shades demanded by the consumer, especially for blonde shades and grey coverage. Such products pose particular difficulties to the manufacturer, as they usually require the use of high levels of oxidising agent typically hydrogen peroxide and ammonia in order to deliver the required lightening effect. However, the presence of oxidizing agent and/or ammonia may in some cases induce mild sensory skin irritation on the scalp that can be described as stinging, tingling, itching, or burning or descriptors there like. Hence, it would also be highly desirable to provide an oxidative hair colouring and/or bleaching composition which delivers the required lightening and/or colour without the aforementioned sensory scalp irritation.

Moreover, in order to provide a product which the consumer can easily apply to the hair without dripping onto the skin, clothes or bathroom surfaces, hair colourant products are designed such that the composition has a certain required viscosity. This is either achieved by providing the dye composition and the oxidizing composition as so called thin-thin type liquid formulations which are thickened upon mixing or where at least one of the components, either the dye composition or the oxidizing composition, is provided as a thickened formulation which thickens the total composition upon mixing. The said thickened formulation can be achieved by the use of a gel network system which provides the desired thickness to either the dye composition or the oxidizing composition or, preferably, both compositions, while often giving additional benefits of cream-like texture, smooth rinse and improved hair feel. Numerous surfactants can be used to formulate gel network thickened composition. However, these surfactants can also further contribute to sensory scalp irritation described above. Hence, it would be further desirable to provide the consumer with a cream hair colourant, providing improved lift and lightening and improved colour delivery, uptake and durability and which is easy to manufacture, delivering the required viscosity and which is shelf life stable, with a minimal amount of associated sensory scalp irritation.

The use of carbonate has been described in the art to reduce the amount of irritating ammonia odour. For example EP 435 012 describes hair-dyeing compositions, which require a short dyeing time, create little damage to hair, and no irritating odour after dyeing comprising a carbonate source, a non odour generating alkali hydrogen peroxide and a buffer solution. Similarly EP 1 106 166 describes hair dye compositions comprising ammonia, carbonate (other than ammonia salt), transition metal salt and chelating agent which do not give off an irritating odour, have low skin irritation and can change the hair colour into a lighter tone in a short time. WO01/28508 describes hair colouring formulations comprising oxidising agents and ammonia carbonate or carbamate which deliver improved bleaching and colouring with reduced odour and hair damage without the need for buffering agents, pH modifiers or hair swelling agents. JP01206825 describes a low pungent hair colouring composition comprising ammonia, ammonium salt and carbonate. US2004/0083557 describes hair colouring compositions comprising an oxidative hair dye precursor, a metal cyanate, an alkalizing agent and an oxidizing agent and preferably a metal bicarbonate salt in order to provide good colour lift and low odour. DE19721797 describes a process to simultaneously dye and lighten hair comprising the steps of applying a composition comprising hydrogen peroxide, water soluble direct dye or oxidative dye, and at least one substance selected from ammonium carbonate, ammonium hydrogen carbonate, sodium carbonate and or sodium hydrogencarbonate.

WO04/014328 describes one step hair colouring compositions comprising peroxide oxidizing agents, specific oxidizing agents and at least one water soluble carbonate releasing salts which more effectively deliver colour wherein the composition is applied for a period of from 2 to 60 minutes. US2004/0098814 describes a method of permanently colouring hair whereby the hair is subjected to a number of consecutive short treatments whereby the treatment comprises a dye intermediate in a shampoo or conditioner base, a water soluble carbonate releasing salt and a water soluble ammonium salt. US2004/0098816 also describes a method for the gradual permanent colouring of hair which includes subjecting the hair to a number of treatments having a set time interval between them, wherein the treatment compositions comprise ammonium carbonate in combination with a chelant.

However it has now been found that the use of hydrogen peroxide and carbonate hair colourant systems, results in additional difficulties in manufacturing. Hence it would be desirable to provide a hair colorant composition which incorporates high levels of carbonate without compromising the product stability or ease of manufacture, with a minimal amount of sensory scalp irritation.

It has now been surprisingly found that oxidative hair colouring compositions comprising an oxidizing agent, an alkaliser and a specific gel network thickening system as defined herein below, preferably utilised with carbonate at pH 9.5 and below, can be formulated as stable thickened cream systems with minimum sensory scalp irritation on application.

Moreover, the compositions exhibit low odour and deliver a high level of lift and lightening equal to the currently utilised ammonia/peroxide systems, whilst reducing the concentration of peroxide and reducing the hair fibre damage. Furthermore, the compositions of the present invention are compatible with current dyes and dye precursor systems and result in improved lift and lightening for blonde shades, excellent dye deposition and colour and improved grey coverage, whilst also being mild to the skin.

SUMMARY OF THE INVENTION

The present invention relates to a hair colouring or bleaching composition comprising two component compositions (i) and (ii), which are mixed prior to application to the hair component (i) comprising:—

1. at least one water soluble source of hydrogen peroxide and 2. at least one gel network thickener system comprising
   (A) at least one non-ionic surfactant and/or amphophile having an HLB of 6 or less and a melting point of at least 30° C. and
   (B) at least one non-ionic surfactant having an HLB of 7 or more,
   wherein the surfactant ratio [b]/[a] is below 0.10, preferably below 0.06, where [a] is the total combined concentration of the surfactants of type (A) expressed as % w/w and [b] is the combined concentration of the surfactants of type (B) expressed as % w/w, and at least 50% w/w of water, and component (ii) comprising at least one alkalizer.

In a further embodiment, the present invention relates to a method of treating hair comprising the steps of applying said composition to the hair, leaving said composition on the hair for from 2 to 60 minutes and subsequently rinsing said composition from the hair.

DETAILED DESCRIPTION OF THE INVENTION

While the specification concludes with claims, which particularly point out and distinctly claim the invention, it is believed the present invention will be better understood from the following description. As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition are used during a treatment, the total weight to be considered is the total weight of all the compositions applied on the hair simultaneously (i.e. the weight found "on head") unless otherwise specified. All ratios are weight ratios unless specifically stated otherwise. All molar concentrations are by volume of the total composition and presented as number of moles of component(s) in one liter of the composition, or "mole/l". When more than one composition are used during a treatment, the total volume to be considered is the total volume of all the compositions applied on the hair simultaneously (i.e. the volume found "on head") unless otherwise specified.

Component Part (i)/Developer

The present invention relates to two component part (i) and (ii) hair dyeing and or bleaching compositions which are mixed together prior to application to the hair. Component part (i), also referred to as the developer, comprises at least one source of an oxidising agent and at least one gel network thickening system as defined hereinafter.

Oxidizing Agent

The compositions according to the present invention comprise or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and or peroxidases may also be used. Mixtures of two or more such oxidizing agents can be used if desired. Preferred for use in the compositions according to the present invention is hydrogen peroxide.

The composition according to the present invention preferably comprises or forms peroxymonocarbonate ions. These ions are typically formed in in-situ from the reaction between a source of hydrogen peroxide and carbonate ions.

According to the present invention the mixed composition of component part (i) and (ii) comprises from about 0.1% to about 10% by weight, preferably from about 1% to about 7% by weight, and most preferably from about 2% to about 5% by weight of an oxidizing agent. Component part (i) thus comprises from about 0.1% to about 20%, preferably from about 1% to about 12%, more preferably from about 4% to about 9% by weight of the oxidizing agent.

Gel Network Thickener

According to the present invention, component part (i) of the hair colouring and bleaching compositions ("developer") comprises a gel network thickener system. The gel network thickener system is defined as a thickening system comprising (A) at least one nonionic HLB surfactant or amphophile having an HLB of 6 or less and having a melting point of at least 30° C., and (B) at least one non-ionic surfactant having an HLB of 7 or more, wherein the surfactant ratio [b]/[a] is below 0.10, preferably below 0.06, wherein [a] is the total combined surfactant (A) concentration and [b] is the total combined surfactant (B) concentration as % w/w and at least 50% water.

The HLB (hydrophilic-lipophilic balance) of the surfactant(s) used according to the invention is the standard HLB according to Griffin defined in publication J. Soc. Cosm. Chem., Vol. 5, 1954, p. 249, the disclosure of which is incorporated herein by reference. The melting point of the surfactant(s) used according to the invention can be measured by a standard melting point method as described in U.S. Pharmacopeia, USP-NF General Chapter <741> "Melting range or temperature". Those skilled in the art will recognize that gel network thickener systems usually have a complex structure of networked lamellar bi-layers and/or vesicles and crystalline phases. These systems usually have creamy appearance and feel and are thus particularly desirable. Without being bound by theory it is believed that gel network thickening system is capable of binding or entrapping various hydrophilic and hydrophobic components of the composition, including water soluble oxidizing agent which can be bound in the inter-lamellar spacing of the gel network system. Such bound materials can be preferentially delivered to and/or through the skin, leading to, in case of the oxidizing agent, increased sensory irritation of the scalp. Surprisingly, it has now been found that by the required specific ratio of the gel network forming surfactants swelling and therefore thickening efficiency can be achieved with very low sensory scalp irritation.

Without being bound by theory, it is believed that the specific ratio of surfactants forming gel network thickener system described in this invention have a particular phase ratio of swollen lamellar and crystalline phases preventing significant entrapment of the water soluble oxidizing agent, while still providing significant viscosity build. Moreover, this system is highly compatible with the high ionic strength systems utilizing e.g. carbonate salts, leading to significant viscosity build upon mixing while providing low sensory scalp irritation in such systems.

According to the present invention, the low HLB non-ionic surfactant or amphophile (A) has an HLB of 6 or less and has a melting point of at least about 30° C. Representative examples of such surfactants include the following compounds (in the examples below "solid" refers to material state at temperature below 30° C.): solid fatty alcohols, solid oxyethylenated fatty alcohols, solid glycol esters, solid oxyethylenated alkyl phenols, solid sorbitan esters, solid sugar esters, solid methyl glucoside esters, solid polyglycerine esters, solid alkyl glyceryl ethers, solid propylene glycol fatty acid esters, cholesterol, ceramides and mixtures thereof.

Preferably the low HLB surfactants (A) are selected from linear or branched fatty alcohols comprising from about 14 to 30 carbon atoms, oxyethylenated fatty alcohols comprising from about 16 to 30 carbon atoms and at most about 2 units of ethylene oxide and glycerol mono esters of fatty acids comprising from about 16 to 30 carbon atoms and mixtures thereof. Most preferably the low HLB surfactants are cetyl, stearyl, cetostearyl or behenyl alcohols, steareth-2 and glycerol monostearate and mixtures thereof.

Surfactant(s) (B) of the gel network thickener system are non-ionic surfactant(s) having an HLB of 7 or more. Non-ionic surfactants suitable for use as surfactant (B) in the gel network thickener system are non-ionic surfactants having an HLB of 7 or more, and preferably comprise one or more polyethyleneoxide chains.

Representative examples of non-ionic surfactants (B) comprising one or more polyethyleneoxide chain include the following compounds: polyoxyethylene alkyl ethers, polyethyleneglycol fatty acid esters, polyoxyethylene castor oil, polyoxyethylene hydrogenated castor oil, polyoxyethylene fatty amides and their momoethanolamine and diethanolamine derivatives and polyethoxylated fatty amines and mixtures thereof.

The preferable non-ionic surfactants comprising one or more polyethyleneoxide chain include polyoxyethylene alkyl ethers, preferably having at least about 10, preferably from about 20 to 200 ethylene oxide units, for example steareth-21, ceteareth-25 and steareth-100, polyethylene glycol fatty acid esters, preferably having at least about 10, preferably from 20 to 200 ethylene oxide units and mixtures thereof.

Also suitable for use as nonionic surfactants (B) are non-ionic surfactants having an HLB of 7 or more which are free of polyethyleneoxide chains. Representative examples of non-ionic surfactants free of polyethyleneoxide chains, include, polyglycerolated fatty acids, polyglycerolated fatty amides, polyglycerolated alkyl phenols, polyglycerolated α-diols, polyglycerolated alcohols, alkyl polyglucosides and sugar esters and mixtures thereof. Preferably, the non-ionic surfactants free of polyethyleneoxide chains are selected from alkyl polyglucosides, sugar esters, polyglyceryl fatty acid esters, alkyl polyglyceryl ethers and mixtures thereof.

According to the present invention the surfactant ratio of the total combined concentration of the surfactants of type (B) expressed as a % weight to the ratio of the total combined concentration of the surfactants of type (A) expressed as a % weight [b]/[a] is below 0.10, preferably below 0.08, even more preferably below 0.06.

Particularly preferred gel network thickening systems according to the present invention include the combination of fatty alcohols comprising from about 16 to 30 carbon atoms or oxyethylenated fatty alcohols comprising from about 16 to 30 and about 2 or less units of ethylene oxide, and polyoxyethylene alkyl ethers having at least about 10, preferably from about 20 to about 100 ethylene oxide units.

More than one surfactant of the above specified types or any combination of the surfactants can be used in the gel network thickening system of the present invention. The composition of the present invention may comprise a total amount of gel network forming surfactants of from about 0.5% to about 30%, preferably from about 1% to about 15%, and more preferably from about 2% to about 10%.

Component Part (ii)

According to the present invention, the composition of the present invention comprises a component part (ii) which comprises at least one alkaliser.

Alkalizer

According to the present invention the part ii) of the composition comprises at least one alkalizer, preferably a source of ammonium ions and or ammonia. Particularly, preferred alkalizing agents are those which provide a source of ammonium ions. Any source of ammonium ions is suitable for use herein. Preferred sources include ammonium hydroxide, ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof. The compositions of the present invention may comprise from about 0.1% to about 20% by weight, preferably from about 0.5% to about 5%, most preferably from about 1% to about 3% of an alkalizing agent, preferably ammonium ions.

According to the present invention the alkaliser preferably comprises at least about 0.1 mole/l preferably at least 0.25 mole/l of a source of carbonate ions or carbamate ions or hydrogencarbonate ions or peroxymonocarbonate ions or any mixture thereof. This amount can be achieved for example by addition of at least about 0.97% (volume percent) of ammonium carbonate (molecular weight equals to 96.09 g/mol) to the composition of invention or, for example, by addition of about 0.5% (volume percent) of Ammonium Carbonate and at least about 0.5% (volume percent) of Potassium Hydrogen Carbonate (molecular weight equals 100.12 g/mor). The compositions of the present invention preferably comprises from about 0.4 mole/l to about 2.0 mole/l, more preferably from about 0.5 mole/l to about 1.5 mole/l of the source of said ions.

Any source of these ions may be utilized. Suitable sources for use herein include sodium, potassium, lithium, calcium, magnesium, barium, ammonium salts of carbonate, carbamate and hydrogencarbonate ions and mixtures thereof such as sodium carbonate, sodium hydrogen carbonate, potassium carbonate, potassium hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate, carbamate and hydrogencarbonate ions are sodium hydrogen carbonate, potassium hydrogen carbonate, ammonium carbamate and mixtures thereof.

In a particularly preferred embodiment of the present invention, the ammonium ion source and the carbonate ion sources are provided by a single source such as ammonium carbonate, ammonium hydrogen carbonate, ammonium carbamate or mixtures thereof. Preferably, if present, the ammonium ions and carbonate ions are present in the composition at a weight ratio of from 3:1 to 1:10, preferably 2:1 to 1:5.

Preferably, the compositions of the present invention have a pH of from about 11.0 to about 7.5, more preferably from about 9.5 to about 8.4 and most preferably from about 9.4 to about 8.5 and even more preferably about pH 9.0.

Additional Components

The compositions of the present invention may further comprise additional ingredients which include, but are not limited to, hair dyeing agents such as oxidative dye precursors, non-oxidative pre-formed dyes, additional thickeners and/or rheology modifiers, solvents, enzymes, additional surfactants, conditioning agents, carriers, antioxidants, stabilizers, chelants, perming actives, perfume, reducing agents (thiolactic acid), hair swelling agents and/or polymers. Some of these additional components are detailed hereafter. These additional components may be present in component part (i) and or component part (ii).

Radical Scavenger

According to the present invention the compositions may comprise a source of radical scavenger. As used herein the term radical scavenger refers to a species that can react with a radical, preferably a carbonate radical to convert the radical species by a series of fast reactions to a less reactive species. The radical scavenger is also preferably selected such that it is not an identical species as the alkalising agent and is present in an amount sufficient to reduce the damage to the hair during the colouring/bleaching process. The compositions of the present invention comprise from about 0.1% to about 10% by weight, preferably from about 1% by weight to about 7% by weight of a radical scavenger.

Preferred radical scavengers are selected from the classes of alkanolamines, amino sugars, amino acids, esters of amino acids and mixtures thereof. Particularly preferred compounds are: momethanolamine, 3-amino-1-propanol, 4-amino-1-butanol, 5-amino-1-pentanol, 1-amino-2-propanol, 1-amino-2-butanol, 1-amino-2-pentanol, 1-amino-3-pentol, 1-amino-4-pentanol, 3-amino-2-methylpropan-1-ol, 1-amino-2methylpropan-2-ol3-aminopropane-1-2-diol, glucosamine, N-acetylglucosamine, glycine, arginine, lysine, praline, glutamine, histidine, sarcosine, serine, glutamic acid, tryptophan, and mixtures thereof and the salts such as potassium, sodium and ammonium salts thereof and mixtures thereof. Especially preferred compounds are glycine, sarcosine, tysine, serine, 2-methoxyethylamine, glucosamine, glutamic acid, morpholine, piperidine, ethylamine, 3-amino-1-propanol and mixtures thereof.

Hair Dyes

The hair compositions of the present invention are preferably hair colouring compositions which comprise oxidative dyeing compositions. Such compositions comprise oxidative hair dye precursors (also known as primary intermediates) that will deliver a variety of hair colors to the hair. These small molecules are activated by the oxidizing agent and react with further molecules to form a larger colored complex in the hair shaft.

The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color. The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are:

1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-aminobenzene (p-AMINOPHENOL), 1-Hydroxynaphthalene (1-NAPHTHOL), 1,5-Dihydroxynaphthalene (1,5-NAPHTHALENEDIOL), 2,7-dihydroxynaphthalene (2,7-NAPHTHELENEDIOL) 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHENOL), 1,2,4-Trihydroxybenzene (1,2,4-TRIHYDROXYBENZENE), 1-Phenol-3-methylpyrazol-5-on (PHENYLMETHYLPYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS (2-HYDROXY-ETHYL)-p-PHENYLENE-DIAMINE), 2,4,5,6-Tetraminopyrimidine (HC Red 16), 1-Hydroxy-3-methyl-4-aminobenzene (4-AMINO-m-CRESOL), 1-Hydroxy-2-amino-5-methylbenzene (6-AMINO-m-CRESOL), 1,3-Bis-(2,4-Diaminophenoxy)propane (1,3-BIS-(2,4-DIAMINO-PHENOXY)-PROPANE), 1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino)benzene, (2-AMINO-4-HYDROXY-ETHYLAMINOANISOLE) 1-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylenedioxybenzene (HYDROXYETHYL-3,4-METHYLENEDIOXY-ANILINE HCl), 2,6-Dihydroxy-3,4-dimethylpyridine (2,6-DIHYDROXY-3,4-DIMETHYLPYRIDINE), 3,5-Diamino-2,6-dimethoxypyridine (2,6-DIMETHOXY-3,5-PYRIDINEDIAMINE), 5,6-Dihydroxyindole (DIHYDROXY-INDOLE), 4-Amino-2-aminomethylphenol (2-AMINOETHYL-p-AMINO-PHENOL HCl), 2,4-Diamino-5-methylphenetol (2,4-DIAMINO-5-METHYL-PHENETOLE HCl), 2,4-Diamino-5-(2'-hydroxyethyloxy)toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl)benzene HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXY-ETHYL-p-PHENYLENEDIAMINE)HCL), 6-Hydroxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5,2-phenyl-3H-pyrazole-3-one, 2-Amino-3-hydroxypyridine (2-AMINO-3-HYDROXYPYRIDINE), 5-Amino-salicylic acid, 1-Methyl-2,6-bis(2-hydroxy-ethylamino)benzene (2,6-HYDROXYETHYLAMINO-TOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHENYLENEDIAMINE), 5,6-Dihydroxyindoline (DIHYDROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYETHYL-4,5-DIAMINOPYRAZOLE SULPHATE). These can be used in the molecular form or in the form of peroxide-compatible salts.

The hair colouring compositions of the present invention may also include non oxidative hair dyes. i.e. direct dyes which may be used alone or in combination with the above described oxidative dyes. Suitable direct dyes include azo or anthraquinone dyes and nitro derivatives of the benzene series and or melanin precursors and mixtures thereof. Such direct dyes are particularly useful to deliver shade modification or highlights. Particularly preferred are Basic Red 51, Basic Orange 31, Basic Yellow 87 and mixtures thereof.

The hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Surfactants

The compositions according to the present invention may further comprise at least about 0.01% of one or more additional surfactants to those utilised in the gel network thickener system. Surfactants suitable for use herein generally have a lipophilic chain length of from about 8 to about 30 carbon atoms and can be selected from anionic, nonionic, amphoteric and cationic surfactants and mixtures thereof.

In one preferred embodiment of the present invention, the component part (ii) of the composition may also comprise a gel network thickening system which may be identical or different to the gel network system comprised in component part (i) of the composition. The preferred gel network thickening system for use therein comprises at least one surfactant or amphophile having an HLB of 6 or less and a melting point of at least 30° C. and at least one surfactant selected from:

a) anionic surfactants according to the formula RnXmYM, wherein R is independently selected from alkyl, alkenyl or alkylaryl groups having from 8 to 30 carbon atoms, X is independently selected from polar groups comprising at least one carbon atom and at least one oxygen or nitrogen atom, Y is an anionic group selected from carboxylates, sulphates, sulphonates or phosphates, n and m are independently 1 or 2, and M is hydrogen or a salt forming cation and mixtures thereof;

b) non-ionic surfactants having an HLB of 7 or more, and comprising one or more polyethyleneoxide chains, wherein each polyethyleneoxide chain has on average at least 50 ethylene oxide units and mixture thereof;

c) non-ionic surfactants having an HLB of 7 or more, which are free of polyethyleneoxide chains and mixtures thereof;

d) cationic surfactants selected from quaternary ammonium salts or amido-amines having at least one fatty chain comprising at least 20 carbon atoms and mixture thereof.

Particularly preferred gel network systems for use in component part (ii) are fatty alcohols, having from 14 to 50 carbon atoms and alkyl ether phosphates having from 1 to 20 ethylene oxide units and mixtures thereof.

Polymers

The composition of the present invention may optionally further comprise at least about 0.01% of a polymer. The polymer can be chosen, for example, from associative polymers, crosslinked acrylic acid homopolymers, crosslinked copolymers of (meth)acrylic acid and of (C1-C6)alkyl acrylate or polysaccharides or mixtures thereof. The polymer may also serve as conditioning agents, as described below. The polymer will generally be used at levels of from about 0.01% to about 20.0% by weight of the composition, preferably from about 0.1% to about 5% by weight of the composition.

Conditioning Agent

The composition of the present invention may comprise or is used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2% by weight of the composition.

Particularly useful conditioning materials are cationic polymers and silicones. Conditioners of cationic polymer type may be chosen from those already known by those skilled in the art as improving at least one cosmetic properties of keratin fibres treated with a cosmetic composition. Cationic polymers can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsiloxane oils, linear polydimethylsiloxane oils containing trimethylsilyl or hydroxydimethylsiloxane endgroups, polymethylphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betain groups. The silicone can either be used as a neat fluid or in the form of an pre-formed emulsion.

In a particularly further preferred embodiment of the present invention, the component part i) of the bleaching and colouring composition comprises at least one cationic polymer.

Chelants

According to the present invention the compositions may comprise chelants. Chelants are well known in the art and refer to a molecule or a mixture of different molecules each capable of forming a chelate with a metal ion.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives and mixtures thereof.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol and mixtures thereof. Finally, the compositions according to the present invention are thus typically provided as an aqueous composition. The compositions of the present invention typically comprise from at least about 10%, preferably from about 20%, more preferably from about 30% and most preferably from about 50% by weight of solvent.

Method of Use

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, a dye component (also called "dye cream" for emulsions or "dye liquid" for solutions) comprising the oxidative dye, precursors and alkalizing agent which is typically ammonia in a suitable carrier and is referred to herein as component ii; a hydrogen peroxide component (also called "hydrogen peroxide cream" for emulsions or "hydrogen peroxide liquid" for solutions or developer) comprising the oxidizing agent (usually hydrogen peroxide) and is referred to herein as component part (i) further comprising the gel network system. The consumer mixes the dye component and the hydrogen peroxide component together immediately before use and applies it onto the hair.

Similarly, bleaching compositions are also usually sold as a kit comprising two or three individually packaged components typically in two or three separate containers. The first container comprises the alkalising agent source (e.g. ammonia and is referred to herein as component ii), the second container comprises the first oxidizing agent and the third (optional) component comprises a second oxidizing agent. The bleaching compositions are obtained by mixing the above-mentioned compositions immediately before use. The gel network system may be comprised with the first or second oxidising agent.

After working the mixture for a few minutes (to insure uniform application to all of the hair), the oxidative dye or bleaching composition is allowed to remain on the hair for an amount sufficient for the dyeing or bleaching to take place (usually from about 2 to 60 minutes, typically about 30 to 45 minutes). The consumer then rinses his/her hair thoroughly with water and allows it to dry. It is observed that the hair has changed from its original color to the desired color.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers. Alternatively the third container can be applied before the oxidative dyeing or bleaching sa a pre-treatment with an optional rinse step.

In another embodiment of the present invention the oxidative hair dye or bleaching compositions may comprise as an optional fourth component a colour refresher composition. Such colour refresher compositions comprise at least one pre-formed dye and may be applied to the hair immediately after the oxidative colour i.e. from about 1 minute after oxidative hair dye or bleach application to 60 days after the application. These colour refresher composition can be used to increase the initial colour obtained and or boost the colour during the wash and style cycle until the next oxidative colouring or bleaching event.

According to the present invention the component parts i) and ii) may be, independently from one another, so called thin liquids or creams. Typically such thin type liquids have a viscosity of less than 1000 cPs. In the preferred embodiment of the present invention, the component part ii) of the composition is a thick cream. Upon mixing the component parts i) and ii), the resultant hair colouring or bleaching compositions according to the present invention preferably have a viscosity of from 1000 to 60000 cPs, more preferably from 2000 to 30000 cPs and most preferably from 3000 to 25000 cPs. Viscosity is measured using Brookfield viscometers with cone and plate attachment. For viscosities in the range of 0-12000 cPs the Brookfield DV-11 viscometer with S42 plate is used. 2 ml sample of the composition is equilibrated at 26.7° C. for three minutes before the readings are taken at 1 rpm. For viscosities in the range of 12,000-60,000 cPs the Brookfield DV-1 viscometer with S52 plate is used. 0.5 ml sample of the composition is equilibrated for 1 minute at 26.7° C. before the readings are taken at 1 rpm.

The present invention also includes embodiments wherein the method of colouring or bleaching the hair comprises applying the composition for at least about 50% of the time period the composition is applied to the hair.

According to the present invention the methods of colouring or bleaching hair also comprise embodiments whereby the composition is applied to the hair and preferably the mixture is worked for a few minutes (to insure uniform application to all of the hair). The composition is then allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with water and allows it to dry and or styles the hair as usual. Such method provides additional convenience to the consumer by permitting a faster colouring or bleaching process.

According to an alternative embodiment of the present invention, the method of colouring and or bleaching the hair is a sequential oxidative hair colouring or hair bleaching method comprising the steps of at least two sequential oxidative hair colour or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes. This method allows consumer to perform colouring or bleaching process in a way similar to conventional hair washing or conditioning process.

The kits described hereinabove are well known in the art and the composition in each container can be manufactured utilizing any one of the standard approaches, these include a) 'Oil in water' process, b) 'Phase Inversion' process and c) 'One-pot' process. For example, when using "oil in water" process, surfactants of the present invention are added to approximately 50% of total water amount of the composition at about 90° C., homogenized for 15 to 30 min, then cooled to room temperature thus forming gel network thickener premix; this premix is then mixed cold with remaining amounts of water, other optional components, oxidizing agent and alkalizer thus forming first or second parts of the above described bleaching or colouring kit.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aerosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

EXAMPLES

The following examples illustrate oxidative dye compositions according to the present invention. It is understood that the examples and embodiments described herein are for illustrative purposes only and that various modifications or changes in light thereof will be suggested to one skilled in the art without departing from the scope of the present invention.

Examples 1-5

Component Part i)

Developer

|  | Surfactant type | 1 | 2 | 3 | 4 | 5 |
|---|---|---|---|---|---|---|
| Ceteareth-25 | B | 0.54 |  | 0.25 |  | 0.16 |
| Steareth-100 | B |  | 0.08 |  | 0.06 | 0.16 |
| Cetyl Alcohol | A | 2.73 |  | 1.65 |  | 3.1 |
| Stearyl Alcohol | A | 2.73 |  | 3.1 |  | 3.1 |
| Steareth-2 | A |  | 3.92 |  | 5.94 |  |
| Hydrogen Peroxide (35% active) | — | 17.14 | 17.14 | 25.71 | 25.71 | 34.29 |
| Polyquaternium-22 (Merquat 295) | — |  |  |  | 0.5 | 0.5 |
| Polyquaternium-37 & Mineral oil (Salcare SC95) | — |  |  |  | 0.5 |  |
| EDTA (tetrasodium salt) | — | 0.05 | 0.05 | 0.05 | 0.05 | 0.05 |
| Etidronic acid | — | 0.2 | 0.2 | 0.2 | 0.2 | 0.2 |
| pH adjust to pH 3.5 | — | qs | qs | qs | qs | qs |
| Water | — | qs | qs | qs | qs | qs |
| Total surfactant type A [a] | — | 5.46 | 3.92 | 4.75 | 5.94 | 6.2 |
| Total surfactant type B [b] | — | 0.54 | 0.08 | 0.25 | 0.06 | 0.32 |
| Ratio [b]/[a] | — | 0.099 | 0.02 | 0.053 | 0.01 | 0.052 |

Examples 6-15

Component Part ii)

| Ingredient | 6 | 7 | 8 | 9 | 10 | 11 | 12 | 13 | 14 | 15 |
|---|---|---|---|---|---|---|---|---|---|---|
| 28% Ammonia | — | — | 7.0 | — | — | — | — | — | 8.0 | — |
| Ammonium Carbonate | 12.0 | — | — | 2.0 | — | — | — | 10.0 | — | — |
| Ammonium Hydrogen Carbonate | — | 6.0 | — | — | 5.0 | 7.0 | 5.0 | — | — | 8.0 |
| Ammonium Carbamate | — | 6.0 | — | — | 5.0 | 7.0 | 5.0 | — | — | 8.0 |
| Potassium Hydrogen Carbonate | — | — | — | 8.0 | — | — | — | — | — | — |
| Sodium Glycinate | 4.0 | — | — | 6.0 | 4.5 | 6.0 | 5.0 | 6.0 | — | 5.0 |
| Crodafos ® CES (Cetearyl alcohol, di-cetyl phosphate & ceteth-10 phosphate) | 8.0 | — | 6.0 | — | — | 8.0 | 4.5 | 5.0 | 6.0 | 10.0 |
| Sodium Palmytoyl Sarcosinate | — | 3.0 | — | — | — | — | — | — | — | — |
| Sodium Alkyl Glyceryl Sulphonate | — | — | — | 3.0 | — | — | — | — | — | — |
| Behentrimonium Chloride | — | — | — | — | 3.0 | — | — | — | — | — |
| Cetyl Alcohol | — | 4.4 | — | 5.0 | 4.0 | — | — | — | — | — |
| Stearyl Alcohol | — | 7.6 | — | 5.0 | 4.0 | — | — | — | — | — |
| p-phenylene diamine | — | — | 1.2 | 0.2 | 1.6 | — | 1.2 | 0.2 | 1.6 | — |
| p-amino phenol | — | 0.6 | — | 0.8 | — | — | — | 0.8 | — | 0.6 |
| 2,5-diaminotoluene sulphate | — | 0.2 | 0.4 | — | — | — | 0.4 | — | — | 0.2 |
| m-aminophenol | — | — | 0.2 | — | 0.4 | — | 0.2 | — | 0.4 | — |
| Resorcinol | — | 1.0 | — | 0.8 | — | — | — | 0.8 | — | 1.0 |
| napthol | — | — | 0.4 | — | 0.06 | — | 0.4 | — | 0.06 | — |
| 4-amino-2-hydroxy toluene | — | 0.4 | — | 0.6 | — | — | — | 0.6 | — | 0.4 |
| Basic red 51 | — | 0.2 | — | — | — | — | 0.4 | — | — | — |
| Basic yellow 87 | — | 0.4 | — | — | — | — | 0.6 | — | — | — |
| Amidomethicone (DCAP 6087) | — | — | — | — | — | — | — | — | — | 0.5 |
| Polyquaternium-22 (Merquat 295) | — | — | — | — | — | — | — | 0.2 | — | — |
| Polyquaternium-37 & Mineral oil (Salcare SC95) | 0.25 | — | — | 0.5 | — | 0.5 | — | 0.4 | — | — |
| Xanthan gum | 0.4 | — | — | — | — | — | — | — | — | — |
| EDTA (tetrasodium salt) | 0.2 | 0.2 | 0.2 | 0.2 | 0.2 | 0.2 | 0.2 | 0.2 | 0.2 | 0.2 |
| Sodium sulphite | 0.2 | 0.2 | 0.2 | 0.2 | 0.2 | 0.2 | 0.2 | 0.2 | 0.2 | 0.2 |
| Ascorbic Acid | 0.2 | 0.2 | 0.2 | 0.2 | 0.2 | 0.2 | 0.2 | 0.2 | 0.2 | 0.2 |
| Propylene Glycol | 3.0 | 3.0 | 3.0 | 3.0 | 3.0 | 3.0 | 3.0 | 3.0 | 3.0 | 3.0 |
| pH adjust to | 9.0 | 9.0 | 10.0 | 9.0 | 9.0 | 9.0 | 9.0 | 9.0 | 10.0 | 9.0 |
| Water | qs | qs | qs | qs | qs | qs | qs | qs | qs | qs |

Component parts i) and part ii) are mixed prior to application on hair and the viscosity of the mixed formulations is within the range of 1000 to 60000 cPs.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A hair colouring or bleaching composition comprising two component compositions, (i) and (ii), which are mixed prior to application to the hair, component (i) comprising:
    at least one water soluble source of an oxidizing agent and at least one gel network thickener system comprising:
    (A) cetyl alcohol and stearyl alcohol having an HLB of 6 or less and a melting point of at least about 30° C. and
    (B) Ceteareth-25 having an HLB of 7 or more, wherein the surfactant ratio [b]/[a] is 0.05, where [a] is the total combined concentration of the surfactants of type (A)

expressed as % w/w and [b] is the combined concentration of Ceteareth-25 expressed as % w/w, and at least about 50% w/w of water, or (C) Steareth-2 having an HLB of 6 or less and a melting point of at least about 30° C. and (D) Steareth-100 having an HLB of 7 or more, wherein the surfactant ratio [b]/[a] is 0.01, where [a] is the total combined concentration of Steareth-2 expressed as % w/w and [b] is the combined concentration Steareth-100 expressed as % w/w, and at least about 50% w/w of water; and component part (ii) comprising at least one alkalizer.

2. A hair colouring or bleaching composition according to claim 1, wherein said composition comprises from about 0.1 to about 10% by weight of said source of an oxidizing agent, from about 0.5 to about 30% by weight of said gel network system and from about 0.1 to about 20% by weight of said alkaliser.

3. A hair colouring or bleaching composition according to claim 1, wherein said component part (i) further comprises at least one cationic polymer.

4. A hair coloring or bleaching composition according to claim 1, wherein said at least one alkalizer comprises at least one source of ammonium ions.

5. A hair colouring or bleaching composition according to claim 1, wherein said at least one alkalizer comprises a source of carbonate ions, carbamate ions, hydrogencarbonate ions or mixtures thereof.

6. A hair coloring or bleaching composition according to claim 1, wherein said composition after mixing said component parts (i) and (ii) has a pH of from about 7.5 to about 11.0.

7. A hair colouring or bleaching composition according to claim 1, wherein said composition after mixing comprises at least one source of radical scavengers.

8. A hair colouring or bleaching composition according to claim 1, wherein said composition after mixing has a viscosity of from 1000 to 60000 cPs.

9. A hair colouring composition according to claim 1, wherein said composition after mixing comprises at least one oxidative dye precursor or at least one pre-formed dye.

10. A hair colouring or bleaching kit comprising i) an individually packaged oxidizing component comprising at least one source of an oxidizing agent and at least one gel network thickener system, comprising (A) cetyl alcohol and stearyl alcohol having an HLB of 6 or less and a melting point of at least about 30° C. and (B) Ceteareth-25 having an HLB of 7 or more, wherein the surfactant ratio [b]/[a] is below 0.10, wherein [a] is the total combined concentration of all surfactants of type (A) and [b] is the total combined concentration of Ceteareth-25 expressed as % w/w, and at least about 50% water, or (C) Steareth-2 having an HLB of 6 or less and a melting point of at least about 30° C. and (D) Steareth-100 having an HLB of 7 or more, wherein the surfactant ratio [b]/[a] is 0.01, where [a] is the total combined concentration of Steareth-2 expressed as % w/w and [b] is the combined concentration Steareth-100 expressed as % w/w, and at least about 50% w/w of water;

ii) an individually packaged second component comprising at least one alkalizer.

11. A method of treating hair comprising the steps of applying a composition after mixing according to claim 1 to the hair, leaving said composition on the hair for from about 2 to 60 minutes and subsequently rinsing said composition from the hair.

12. A method of treating hair comprising the steps of applying a composition after mixing according to claim 10 to the hair, leaving said composition on the hair for from about 2 to 60 minutes and subsequently rinsing said composition from the hair.

13. A method according to claim 11, wherein said composition is retained on the hair for a time period of less than about 20 minutes.

14. A method according to claim 12, wherein said composition is retained on the hair for a time period of less than about 20 minutes.

15. A method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition according to claim 1, applying said composition to the hair and retaining said composition on the hair for a time period of less than about 20 minutes and subsequently rinsing said composition from the hair.

16. A method of sequential oxidative hair colouring or hair bleaching comprising the steps of at least two sequential oxidative hair colour or hair bleaching treatments, wherein the time period between each treatment is from 1 day to 60 days, and wherein each treatment comprises the steps of providing a composition according to claim 10, applying said composition to the hair and retaining said composition on the hair for a time period of less than about 20 minutes and subsequently rinsing said composition from the hair.

* * * * *